(12) United States Patent
Frutos et al.

(10) Patent No.: US 6,579,680 B2
(45) Date of Patent: Jun. 17, 2003

(54) METHOD FOR LABEL-FREE DETECTION OF HYBRIDIZED DNA TARGETS

(75) Inventors: Anthony Glenn Frutos, Painted Post, NY (US); Joydeep Lahiri, Painted Post, NY (US); Santona Pal, Painted Post, NY (US); Mark A. Quesada, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/795,158

(22) Filed: Feb. 28, 2001

(65) Prior Publication Data

US 2002/0001844 A1 Jan. 3, 2002

Related U.S. Application Data

(60) Provisional application No. 60/185,329, filed on Feb. 28, 2000.

(51) Int. Cl.[7] ............... C12Q 1/68; C12P 19/34; C12M 1/34; C07H 21/02; C07H 21/04
(52) U.S. Cl. ............... 435/6; 435/7.1; 435/91.1; 435/91.2; 435/287.2; 536/22.1; 536/23.1; 536/24.3; 536/24.31; 536/24.32; 536/24.33
(58) Field of Search ............... 435/6, 7.1, 91.1, 435/91.2, 287.2; 536/22.1, 23.1, 24.3–24.33

(56) References Cited

U.S. PATENT DOCUMENTS

| | | | |
|---|---|---|---|
| 5,780,233 A | 7/1998 | Guo et al. | 435/6 |
| 5,925,517 A | 7/1999 | Tyagi et al. | 435/6 |
| 5,942,609 A * | 8/1999 | Hunkapiller et al. | 536/25.3 |
| 6,248,521 B1 * | 6/2001 | Van Ness et al. | 435/6 |

FOREIGN PATENT DOCUMENTS

| | | |
|---|---|---|
| JP | 10-262675 | 10/1998 |
| WO | WO 99/21881 | 5/1999 |

OTHER PUBLICATIONS

Li et al NAR vol. 30 No. 2 e5 pp. 1–9 2002.*

Fang et al., Designing a Novel Molecular Beacon For Surface–Immobilized DNA Hybridization Studies, J. Am. Chem. Soc. 1999, 121, 2921–2922.

Liu et al., A Fiber–Optic Evanescent Wave DNA Biosensor Based on Novel Molecular Beacons, Anal. Chem., 1999, 71, 5054–5059.

Tyagi et al., Molecular Beacons: Probes the Fluoresce Upon Hybridization, Nature Biotecnhology, vol. 14, Mar. 1996, pp. 303–308.

Frutos et al., Method For Detection of Single–based Mismatches Using Bimolecular Beacons, Journal of the American Chemical Society, vol. 124, No. 11, pp. 2396–2397.

Sanjay Tyagi et al., "Molecular Beacons: Probes that Fluoresce Upon Hybridization", Nature Biotechnology, vol. 14, Mar. 1996, pp. 303–308.

(List continued on next page.)

*Primary Examiner*—Jeffrey Siew
(74) *Attorney, Agent, or Firm*—Vincent T. Kung (57) ABSTRACT

A method for the detection and analysis of genetic polymorphisms using arrays that do not require labeling of a target nucleic acid sequence. Hybridization of a perfectly complementary nucleic acid target sequence to an oligonucleotide probe sequence results in a displacement and complete removal of a hybridized probe sequence from the same oligonucleotide probe sequence by means of a thermokinetic reaction. The removal of the hybridized probe sequence, having a quencher element, increases the intensity of emission by an emitter element on the oligonucleotide probe sequence.

36 Claims, 5 Drawing Sheets

OTHER PUBLICATIONS

Zhen Guo et al., "Enhanced Discrimination of Single Nucleotide Polymorphisms by Artificial Mismatch Hybridization", Nature Biotechnology, vol. 15, Apr. 1997, pp. 331–335.

Sanjay Tyagi et al., "Multicolor Molecular Beacons For Allele Discrimination", Nature Biotechnology, vol. 16, Jan. 1998, pp. 49–53.

Xiaojing Liu et al., "A Fiber–Optic Evanescent Wave DNA Biosensor Based on Novel Molecular Beacons", Analytical Chemistry, 1999, pp. A–F.

Gregoire Bonnet et al., "Thermodynamic Basis of the Enhanced Specificity of Structured DNA Probes", Proc. Nat. Acad. Sci. USA, vol. 96, pp. 6171–6176, May 1999, Biophysics.

Xiaohong Fang et al., "Designing a Novel Molecular Beacon for Surface–Immobilized DNA Hybridization Studies", J. Am. Chem. Soc., 1999, vol. 121, pp. 2921–2922.

Frank J. Steemers et al., "Screening Unlabeled DNA Targets With Randomly Ordered Fiber–Optic Gene Arrays", Nature Biotechnology, vol. 18, Jan. 2000, pp. 91–94.

* cited by examiner

FIG. 1A

◯ = abasic site   Ⓓ = emitter (Donor)   Ⓐ = quencher (Acceptor)

◯ = abasic site   Ⓓ = emitter (Donor)   Ⓐ = quencher (Acceptor)

No
Quencher
(High Signal)

FIG. 3B

Bind
Quencher
(Decreased Signal)

FIG. 3C

Remove
Quencher
(High Signal)

FIG. 4

↓ Bind quencher

↓ Add unlabeled "X" complement

FIG. 5

METHOD FOR LABEL-FREE DETECTION OF HYBRIDIZED DNA TARGETS

CLAIM OF PRIORITY

This Application claims priority of U.S. Provisional Application No. 60/185,329, filed on Feb. 28, 2000.

FIELD OF THE INVENTION

The invention relates to the field of molecular biology, and more particularly to the field of assays that involve nucleic acid hybridization probes. Hybridization assays are employed in the detection and identification of specific nucleic acid sequences in genes, or RNA molecules, for analysis of gene expression and genetic polymorphisms. Such assays are used for medical diagnostics, as well as in pharmacological, food technology, agricultural, and biological research.

BACKGROUND

Numerous methods have been used for detecting variation in nucleic acid sequence. These methods include, for example, electrophoretic mobility shifts due to conformational changes induced by single or multiple base variation, and direct mass spectrometric sequence determination. Yet, among these varied methods, hybridization techniques are particularly well suited to detect specific target sequences in a complex mixture where nucleic acid hybridization probes are used. These hybridization techniques can be broadly classified as being either homogeneous or heterogeneous assays.

Sometimes referred to as homogeneous assays, several solution-phase detection schemes have been developed. By "homogeneous" we mean assays that are performed without separating unhybridized targets from probe-target hybrids. These schemes often make use of the fact that the immediate chemical environment can affect the fluorescence of many fluorescent labels. Oligonucleotide probes that are complementary to contiguous regions of a target DNA strand are employed. One probe contains a fluorescent label on its 5' end and the other probe contains a different fluorescent label on its 3' end. Upon hybridization to contiguous regions on a target sequence, the 5' and 3' ends of the probes are brought in close proximity, such that one quenches the fluorescence of the other. When the sample is stimulated by light of an appropriate frequency, fluorescence resonance energy transfer ("FRET") from one label to the other occurs. This energy transfer produces a measurable change in spectral response, indirectly signaling the presence of the target. The labels are sometimes referred to as FRET pairs. The altered spectral properties can be subtle, and the changes, if one is not careful, can be small relative to background signal. This characteristic can be seen as a potential shortcoming of this type of hybridization. Although this technique works well with a small number of samples, the relatively limited, low through-put of homogeneous hybridization, however, can be another potential shortcoming, since homogeneous assays are not as amenable to high volume genetic processing as an array.

Recently, so-called molecular beacons have been developed and used to detect the presence of unlabeled target sequences in homogeneous solution. Molecular beacons are oligonucleotides that possess a hairpin structure in which the loop portion of the molecule is a probe sequence that is complementary to a target sequence in the nucleic acid to be detected, and the stem is formed by the annealing of complementary arm sequences. (For instance, U.S. Pat. No. 5,925,517, entitled "Detectably Labeled Dual Conformation Oligonucleotide Probes, Assays and Kits," issued to Tyagi et al., describes one form of molecular beacon, while PCT International Publication No. WO 99/21881 entitled "Methods, Kits, and Compositions Pertaining to Linear Beacons," by Gildea et al. discloses another form. Pertinent content of these two patent documents is incorporated herein by reference.) A fluorophore is covalently attached to the end of one arm and a quencher dye is covalently attached to the end of the other arm. The stem keeps the fluorophore-quencher pair in close proximity to each other, thereby quenching the fluorescence of the fluorophore. Only upon hybridization to a perfectly matched, that is, completely complementary, target nucleic acid sequence is the hairpin-stem structure disrupted, resulting in a fluorescence signal. Due to the constrained nature of the hairpin structure, molecular beacons can recognize their perfect complementary sequence with enhanced specificity compared to their linear counterparts. Thus, molecular beacons have been used to easily discriminate between targets that differ from one another by even only a single nucleotide.

Although effective, the use of molecular beacons also has some drawbacks. Because hairpin formation and stability is critically dependent upon oligonucleotide sequence, molecular beacons can be difficult to design. As a consequence, several preliminary experiments need to be conducted to ensure the proper formation and stability of the hairpin structure. These additional activities add to both the time and expense of the assay. Until very recently, molecular beacons have been used only in homogeneous solutions. In addition, like other homogeneous assays, molecular beacon techniques also suffer from limited, low through-put hybridization and analysis. To be used in large-scale parallel analysis, molecular beacons must be attached to a solid surface. Attachment of these hairpin structures on a surface while maintaining proper fluorescence, quenching, and hybridization has, however, proven to be non-trivial, if not difficult, due to steric effects of the substrate on the hairpin.

For large-scale, parallel analysis of target DNA sequences, workers look to array technology. High through-put hybridization analysis has been achieved with the advent of DNA microarrays, also known as DNA "chips", which permit the possibility of applying high probe densities on small substrates. A typical DNA chip experiment uses a conventional, heterogeneous, hybridization assay. Heterogeneous hybridization typically comprises a number of steps: immobilizing probe nucleic acid sequences on paper, beads, or plastic surfaces, adding an excess of labeled targets that are complementary to the sequence of the probe: hybridizing; removing excess labeled targets and unhybridized targets, and detecting the targets that remain bound to the immobilized probes. Unhybridized targets are removed by washing of the hybrids. In experiments such as these, careful control of both surface chemistry and washing conditions is required to minimize background signal from the nonspecific adsorption of labeled target sequences.

Recently a heterogeneous, nucleic acid hybridization assay that enhances discrimination of single nucleotide polymorphisms (SNPs) has been reported in the scientific literature—a paper entitled "Enhanced Discrimination of Single Nucleotide Polymorphisms by Artificial Mismatch Discrimination," *Nature Biotechnology*, 15, 331–335 (1997), the relevant sections of which are incorporated herein by reference. Developed by Z. Guo et al., this process is based on differences in thermodynamic stability of duplexes formed by an oligonucleotide containing an artificial mismatch site and two different labeled targets. From this work, U.S. Pat. No. 5,780,233, entitled "Artificial Mismatch Hybridization," was issued to Guo et al, (the '233 Patent). The pertinent content of the '233 Patent is incorporated herein by reference. This patent describes a process for hybridizing labeled first and second target sequences to an immobilized oligonucleotide. The immobilized oligonucleotide has a nucleic acid sequence that is complementary in part to both the first and second targets, including at the position of sequence variation, but comprises at least one "artificial" mismatch relative to the first target, and an "artificial" mismatch and a "true" mismatch relative to the second target. The oligonucleotide forms a first duplex and a second duplex with the first and second targets, respectively, wherein the first duplex has a melting temperature that is higher than that of the second duplex.

Even though the process described by Guo et al. has potential advantages, it still may not possess the degree of sensitivity required for certain applications, or as workers in the field may wish to achieve. Primarily, the problem with the method by Guo et al. is that it still requires labeled target sequences. Non-specific binding of targets with probe moieties increases background signals and prevents discrimination between sample targets, hence resulting in lower sensitivity. Further, labeling can be both time consuming and costly.

In view of the current situation, a need exists for a new method that combines the advantages of a molecular beacon system (unlabeled targets, enhanced specificity) while simplifying the attachment of nucleic acid probes to surfaces. The present invention addresses and satisfies all of these needs and provides other additional advantages as will be described below.

SUMMARY OF THE INVENTION

The invention comprises an improved method for detecting and analyzing genetic polymorphisms using arrays that do not require labeling of the target nucleic acid sequence. The method employs, in part, a set of first oligonucleotide probes, each of which has a nucleic acid sequence that is attached to a solid support, and differs from each other in at least one specific base location. The method further uses a set of hybridized, second oligonucleotide probes, each of which has a complementary nucleic acid sequence to a first oligonucleotide probe, and each of the nucleic acid sequences of the hybridized, second probes incorporates at least one mismatch site. Each first oligonucleotide probe is labeled with an emitter molecule, and each hybridized, second probe with a quencher molecule. An unlabeled sample nucleic acid target is hybridized to the oligionucleotide probe, wherein the sample nucleic acid target displaces the hybridized probe from the oligonucleotide probe to cause the emitter molecule to increase its emission with such displacement. Removal of the corresponding quencher molecule is believed to be accomplished by a process of competitive hybridization that can be assisted by modification of certain hybridization conditions, such as temperature and use of denaturants, such as formamide, that are known by those in the art to increase the stringency of hybridization.

The method, in one embodiment, is based on disrupting fluorescence resonance energy transfer (FRET) between adjacent fluorophores attached on either side of a duplex by competitive hybridization. Enhanced discrimination between perfectly matched sequences and sequences containing a single nucleotide polymorphism (SNP) is achieved by the incorporation of at least one artificial mismatch (i.e. 5-nitroindole, 3-nitropyrole, abasic site) in the quencher probe initially hybridized to the surface-immobilized probe sequences. The invention is also a method for determining whether a nucleic acid target in a sample contains a sequence variation of interest. The invention can widely apply to numerous hybridization-based assays in forensics, genetic analysis, and medical diagnosis in addition to SNP detection.

In another embodiment, the method entails immobilizing on a solid support a plurality of first oligonucleotide probes, where each oligonucleotide probe has a first nucleic acid sequence to which an emitter, such as a fluorescing moiety of a FRET pair, is terminally attached. An unlabeled nucleic acid sample or target, and a second oligonucleotide probe with a second nucleic acid sequence, having at least one artificial mismatch site, are hybridized to the first oligonucelotide probe. The second probe also has a quencher element terminally attached to its nucleic acid sequence. During hybridization, the second probe binds to the first oligonucleotide probe when the sample nucleic acid target is not complementary. As a result, the quencher element on the second probe reduces an emission from the emitter element on the first oligonucleotide probe.

The invention also comprises an article that employs an embodiment of the improved method. The article can be an array for detecting genetic polymorphisms without the need for labeling of the target nucleic acid sequences. Further, the invention includes a biological analysis kit containing such an array.

BRIEF DESCRIPTION OF THE DRAWINGS

FIG. 1 is a schematic illustration of one embodiment of the present invention showing:

(a) a set of oligonucleotide probes, each labeled with an emitter molecule, immobilized on a solid surface, having a hybridized, complementary probe labeled with a quencher molecule bound to each oligonucleotide probe;

(b) an unlabeled nucleic acid target strand hybridizes;

(c) displacement of the hybridized probe by the unlabeled target, resulting in an increase in emission from the emitter molecule.

FIG. 3 is a series of fluorescent scanned images showing three panels of an array having emitter-labeled oligonucleotides immobilized thereon, under the following conditions:

(a) The array as seen with no quencher moiety (high signal);

(b) The array as seen with quencher probe bound to labeled oligonucleotides;

(c) The array as seen after removal of the quencher probes.

DESCRIPTION OF THE INVENTION

For purposes of this patent application, a "nucleic acid target" can be a chromosome or any portion thereof, or can be a recombinant nucleic acid molecule, such as a plasmid, oligonucleotide, or other nucleic acid fragment, and may be naturally occurring or synthetic. The target length is not critical provided that the target is sufficiently long to complement the probe, as described herein. When the target is DNA, it is understood that the DNA is provided for use in the method in a partially denatured or single stranded form, capable of hybridizing to a single-stranded oligonucleotide probe.

"Complementary" nucleic acid sequences are nucleotides on opposite strands that would normally base pair with each other. A "mismatch" is found at any position where no direct Watson-Crick-base pair (A/T, G/C, C/G, T/A) correspondence exists between the oligonucleotide and the target in the region of complementarity between the two strands. An artificial mismatch is typically provided at one or more positions in an oligonucleotide, but can also include more extensive changes.

A standard method of detecting a variation in a nucleic acid sequence depends on specific recognition by one oligonucleotide strand of a complementary nucleic acid target strand. In a conventional, heterogeneous hybridization assay, a set of fluorescently labeled targets is hybridized to an array of probe DNA molecules attached to a surface. After hybridization has been completed, the surface is washed to remove any excess labeled targets and then scanned in a fluorescence imager. The presence of a fluorescence signal at a given array location indicates the formation of a DNA duplex.

The present invention differs in at least one aspect from conventional heterogeneous assays in that the inventive method employs unlabeled sample target sequences. Additionally, the present invention employs a displacement mechanism of hybridized probes that contain at least one artificial mismatch site. Such displacement is accomplished by a principle of thermo-kinetic and competitive hybridization.

When the probe and the target are not completely complementary to each other, the affinity of the two strands for one another is reduced. Reduced affinity is manifest by a decrease in duplex thermal stability, which can be conveniently monitored by measuring the duplex melting temperature ($T_m$). The difference in duplex melting temperatures ($\Delta T_m$) between, on the one hand, a perfectly matched probe and target and, on the other hand, the same probe with a second target that differs from the first target in at least one base location has proven to be useful in detecting sequence variations in DNA. In comparison, a method for detecting sequence variations that relies merely on the melting temperatures of duplexes, without more, is not as sensitive as fluorescence based techniques, nor is it amenable to high volume screening or analysis. The present invention incorporates the benefits of both a thermo-kinetic displacement and fluorescence.

Figure 1A:
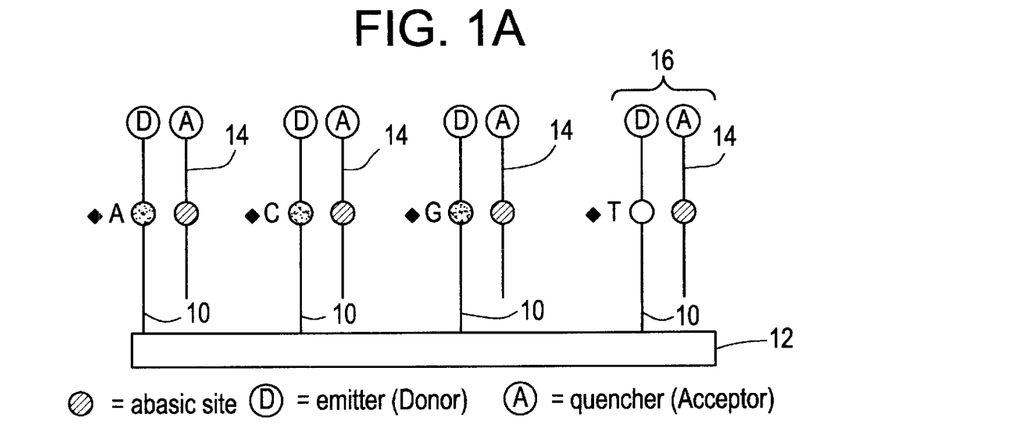
Figure 1B:
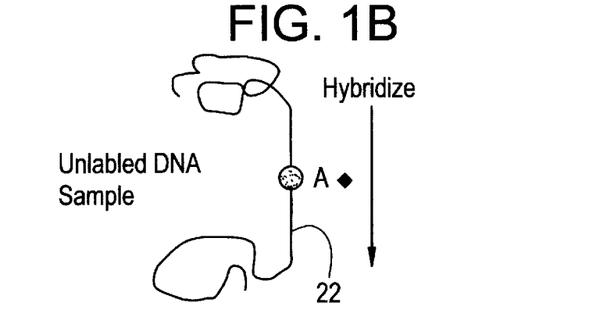
Figure 1C:
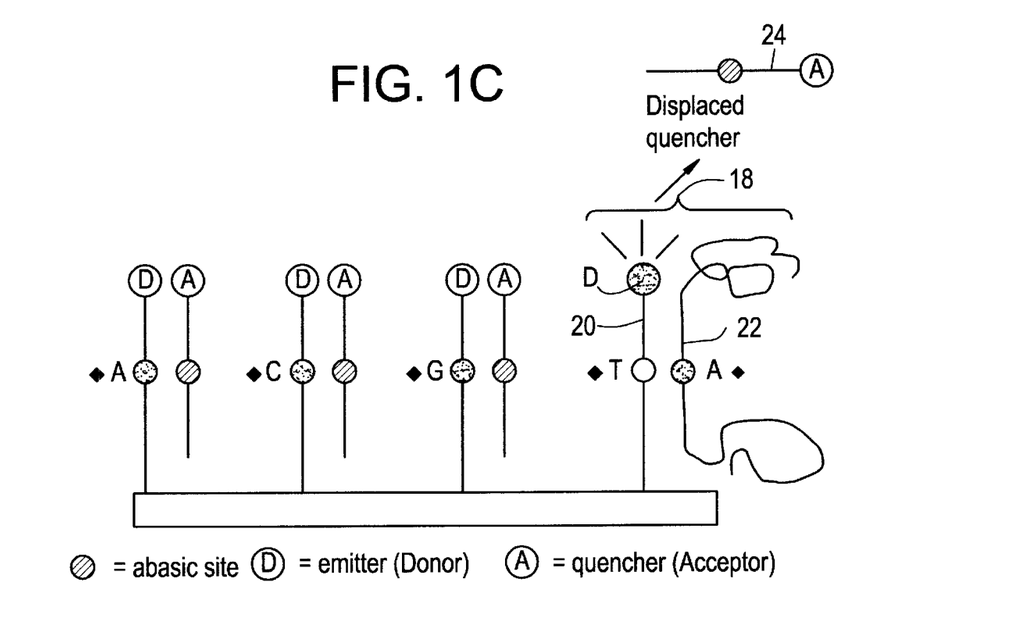

FIGS. 1(a)–(c) illustrate the basic concept and design of the invention. A set of oligonucleotide probes (10) comprising four different nucleic acid sequences differing from each other at a specific base location (A, G, C, T) are covalently attached to a solid support (12). These probes (10) each are labeled with an emitter molecule (D), such as a fluorophore in a FRET system, whose emission or fluorescence is initially quenched by the presence of a hybridized, complementary probe (14) labeled with a quencher molecule, such as a FRET acceptor (A). (Note that D and A could be any number of FRET donor-acceptor pairs.) Incorporated in the nucleic acid sequence, either near the center or at an end, of the quencher probe (14) is at least one mismatch site that destabilizes the duplex (16) relative to a perfectly matched duplex (18) and facilitates single-base mismatch discrimination. The mismatch is preferably an artificial mismatch. Several types of artificial mismatches have been developed and used as primers for dideoxy sequencing and polymerase chain reactions (PCR), including abasic sites, as shown in FIG. 1, and universal base analogs such as 3-nitropyrole and 4-, 5-, and 6-nitroindole. Although Guo et al. reported that 3-nitropyrole was incorporated into oligonucleotides to enhance discrimination of SNP detection in labeled assays, the use of artificial mismatches in an unlabeled, competitive binding assay, as described here, however, has not been previously reported.

In one embodiment, a user interested in determining the presence or absence of a SNP at the location of interest would hybridize an unlabeled (PCR) target sequence (22) to the surface shown in FIG. 1(a). Hybridization of this target sequence to the perfectly matched complementary probe sequence (20) on the surface displaces the less stable quencher probe (24), resulting in an increase in fluorescence signal at the array location, as seen in the sequence of events depicted in FIGS. 1(b) and (c). Because little or no displacement occurs to the other probes containing a single-base mismatch, the quencher probe continues to bind with the oligonucleotide probe, and fluorescence continues to be quenched. In the probes having a nucleotide mismatch, no enhancement in signal is observed. This feature of the process improves the ability of researchers to detect and discriminate with greater specificity the nucleic acid sequences of genetic samples in which they have interest.

One must bear in mind that in practice the precise amount of immobilization of the four probe oligonucleotides may be difficult to control, and complete hybridization to all of the immobilized oligonucleotides may be difficult to achieve. The amount of hybridization of target sequences to immobilized oligonucleotides is strongly influenced by specific surface attachment chemistry that can be modified to achieve maximum hybridization efficiency. For example, controlled densities of surface carboxylic acid groups have been used for ligand coupling, as disclosed in U.S. patent application Ser. No. 09/704,013, "Polymer Support for DNA Immobilization," by J. Lahiri et al., incorporated herein by reference. Despite optimized surface attachment chemistry, the hybridization efficiency likely will be less than 100%. As a result, residual fluorescence will likely persist even after hybridization of the quencher probe to the labeled targets, with the values of the residual fluorescence varying from spot to spot. Therefore, SNP discrimination would be based on a comparison of the ratios of the fluorescence before and after competitive hybridization of the unlabeled probe to the different target sequences.

For the specific application described here, the stabilities of the different nucleic acid duplexes, in decreasing order of stability, should ideally be: a perfect match>mismatch due to quencher probe>mismatch due to SNP. In other words, a perfect match is most stable and preferred, next an artificial mismatch in the sequence of the probe labeled with the quencher moiety, and then finally a mismatch in the unlabeled, sample nucleic acid target. To realize this, the design of the artificial mismatch must be considered carefully. Table I presents the results of a series of thermal melting experiments performed in solution using 15 base pair oligonucleotides of the following design:

5'-GGG CTA TXA CTA TAG-3' (SEQ IN NO: 1)
3'-CCC GAT AQT GAT ATC-5' (SEQ IN NO: 2)

in which X and Q were varied to produce either natural (A/C, G/T) or artificial (G/5-nitroindole, G/abasic site) mismatches.

TABLE 1

Melting temperatures ($T_m$) for DNA oligonucleotides containing either natural or artificial mismatches. Measurements were made in a pH 7 buffer consisting of 10 mM phosphate. 1 mM EDTA and 1 M NaCl.

| Duplex | $T_m$ (° C.) |
| --- | --- |
| perfect match | 63.3 |
| G-T mismatch | 51.1 |
| 5-nitroindole | 50.3 |
| A-C mismatch | 47.9 |
| abasic | 42.8 |

Notice that the 5-nitroindole containing duplex is more stable than the A-C mismatched duplex but is less stable than the perfectly matched duplex. In contrast, the duplex containing an abasic site was the least stable of all. For the invention, the thermodynamic stability of the duplex formed by the hybridization of a perfectly complementary target sample sequence and oligonucleotide probe sequence is greater than the stability of the duplex formed by the same probe sequence and a hybridizable probe containing at least one artificial mismatch site.

A single-base mismatch between the quencher probe and the perfectly matched, unlabeled target possibly may be insufficient for displacing the quencher probe from the immobilized oligonucleotide probe. Nonetheless, this issue can be easily addressed by using a shorter quencher probe, which would reduce the strength of the interaction between the quencher probe and the target. Alternatively, additional mismatch sites could be incorporated into the sequence of a quencher probe. The length of the quencher probe would be optimized to enhance the displacement of the quencher by the perfectly matched, unlabeled target without compromising the stringency of SNP discrimination. Other possible methods to optimize displacement without compromising SNP discrimination include the incorporation of different combinations of FRET dyes at different positions of the duplex and the use of multiple artificial mismatches in the sequence of the quencher.

To investigate this displacement issue, we performed a series of solution reactions. Table 2 shows the results of these experiments in which displacement of a quencher oligonucleotide (i.e. dabcyl (Dab) labeled and containing either 5-nitroindole or an abasic site) hybridized to a Cy3 labeled complement, as depicted below, was monitored:

5'-Cy3-GGG CTA TAA CTA TAG-3' (SEQ ID NO: 3)
3'-Dab-CCC GAT AXT GAT ATC-5' (SEQ ID NO: 4)
X=5-nitroindole or abasic site Displacement of the quencher oligonucleotide was attempted using a two-fold excess of either a single base (A-C, G-T) mismatch or perfectly complementary unlabeled sequence and was monitored by the increase in fluorescence intensity of the Cy3 dye.

TABLE 2

Results of solution displacement reactions.

| 5-nitroindole | |
| --- | --- |
| Initial fluorescence intensity: | 1 |
| Single base mismatch: | 1.4 |
| Perfect match: | 2.15 |
| abasic | |
| Initial fluorescence intensity: | 1 |
| Single base mismatch: | 2 |
| Perfect match: | 2.4 |

Notice that single-base mismatch discrimination was achieved with both the 5-nitroindole and the abasic site. As expected, however, based on the solution Tm experiments as shown in Table 1, 5-nitroindole was better at discriminating single-base mismatches than the abasic site. These results also indicate that, for solution-based experiments, a single-base artificial mismatch is more than sufficient to allow displacement by a perfectly matched oligonucleotide target. As described in the previous paragraph, the ease of displacement can be mediated by changing the length of the quencher probe and immobilized probe and/or by varying the concentration of the displacing sample target. To promote displacement of 5-nitroindole mismatched sequences, the stringency of conditions could be enhanced by employing an increase in the concentration of formamide or increase temperature from room temperature to 45–55° C.

Different from prior art in that it involves displacement of an artificial mismatch sequence by using unlabeled nucleotide targets and labeled probes, the advantages of this invention are varied. First, the end user does not need to label a target molecule of interest. One can use unlabeled samples. This reduces the potential influences from steric and chemical interaction caused by the label on the raw nucleic acid sequence, which can save time and expenses for the end user. Second, because the target sequences are unlabeled, background signal due to any nonspecific absorption is reduced substantially, if not eliminated. If the assay already has an initial low signal eliminating background signal, this feature is especially beneficial to distinguishing target sequences of interest. Third, the use of at least one artificial mismatch site permits for easier discrimination between perfectly matched and single or multiple-base mismatched DNA duplexes. The invention increases the hybridization sensitivity, facilitates the recognition of mismatch and improves the accuracy of nucleic acid base sequence analysis.

So, to reiterate, the invention embodies a method for detection and analysis of genetic polymorphisms. The method comprises providing (1) a set of oligonucleotide probes and (2) a set of hybridized probes. Each of the oligonucleotide probes has a nucleic acid sequence that is attached to a solid support, and differs from each other with respect to at least one specific base (mismatch site) at a location along the sequence. Each of the hybridized probes has a nucleic acid sequence that is complementary to a corresponding oligonucleotide probe. Each of the nucleic acid sequences of the hybridized probe incorporates at least one artificial mismatch site. Each oligonucleotide probe is labeled with an emitter element, and each hybridized probe is labeled with a quencher element. An unlabeled sample nucleic acid target is hybridized to an oligionucleotide probe, wherein the sample nucleic acid target displaces the hybridized probe from the oligonucleotide probe to which the hybrid probe is bound. This displacement occurs only from those probes to which the unlabeled sample is perfectly complementary. With the displacement of the quencher element, the emitter element increases its emission.

The hybridized probes contain 1–5 artificial mismatch sites, and each artificial mismatch is separated from one another by, about 3–5 nucleotide positions. The oligonucleotide probes are preferably attached to a solid support by covalent bonding, but are also capable of being attached to a solid support by non-covalent bonding, such as ionic or hydrogen bonds. The solid support (12) can be an article in the form of porous or non-porous substrates, three-dimensional surfaces, beads or planar surfaces, and made from materials such as glass, polymers, plastics, metals, and silicon. The nucleic acid sequences of both oligonucleotide probes and hybridized probes each have a functional length of up to about 20–25 nucleotides, with a preferred functional length of about 14–19 nucleotides. The oligonucleotide probe sequences are selected from the group consisting of DNA, PNA, RNA, and mixtures of DNA, PNA and RNA.

The sample nucleic acid target should be complementary or perfectly matched to at least one species of a number of oligonucleotide probes. The sample nucleic acid target is favored to react with a perfectly matched oligonucleotide probe to displace a corresponding hybridized probe by a thermo-kinetic mechanism. The duplex formed by hybridizing a sample nucleic acid target to an oligonucleotide probe has a melting temperature ($T_m$) greater than the melting temperature of a duplex formed by the same probe sequence with another nucleic acid sequence having an artificial mismatched site.

Alternatively, in a particular embodiment, the method includes a plurality of DNA duplexes. Each of these duplexes is formed by a first nucleic acid sequence that is immobilized to a solid support and labeled with a fluorophore, and a complementary, second nucleic acid sequence that incorporates at least one mismatch site and labeled with a fluorescence quencher. The solid support, having the first nucleic acid sequence immobilized thereon, is exposed in solution to a sample DNA sequence. The sample DNA sequence preferentially dislodges from the first nucleic acid sequence, to which the sample DNA sequence is perfectly complementary, the corresponding second nucleic acid sequence in the DNA duplex, thereby removing the quencher. The sample DNA target hybridizes with the first nucleic acid sequence at a temperature that ranges from about 20° C. to 100° C. or more preferred at about 22° C. or 25° C. to about 45° C. or 55° C.

The invention also includes an article for detecting or identifying genetic polymorphisms, such as an array or a multi-well microplate, with a configuration of 96, 384, 576, or more wells. At least a set of oligonucleotide probes is prepared or immobilized on the article. Alternatively, an array can have prepared both a set of olgionucleotide probes immobilized on the substrate and a set of hybridized probes bound to the oligonucleotide probes. Each of the oligonucleotide probes has a nucleic acid sequence that is immobilized to the solid support of the array and differs from each other by least one specific base. The set of oligonucleotide probes and corresponding hybridized probes can be pre-selected, prepared, and deposited onto the array. As described above, each of the hybridized probes is labeled with a quencher element and has a complementary nucleic acid sequence to a corresponding oligonucleotide probe. Each of the nucleic acid sequences of said hybridized probes incorporates at least one artificial mismatch site. As detailed above, hybridization of a perfectly complementary, unlabeled sample nucleic acid target sequence is visually indicated, as seen under a predetermined wavelength of light, when the intensity of emission by the emitter element increases. This increased intensity occurs when the quencher element attached to the corresponding hybridized probe is displaced by the unlabeled sample nucleic acid target.

Furthermore, the invention includes a kit suitable for performing an assay that detects the presence, absence, or amount of a sample target nucleic acid sequence. The kit comprises an array with oligonucleotides immobilized thereon, like that described above. In one version, the kit also includes a separate reagent solution containing hybridizable probes, each having a nucleic acid sequence with at least one artificial mismatch site and a quencher element. In other version, a hybridized duplex of a first nucleic acid sequence of the oligonucleotide probe and a complementary second nucleic acid sequence, with at least one artificial mismatch site and a quencher element, is already immobilized on the array. The invention reduces the difficulty of dislodging the hybridized, quencher probe.

EXAMPLES

Figure 2:
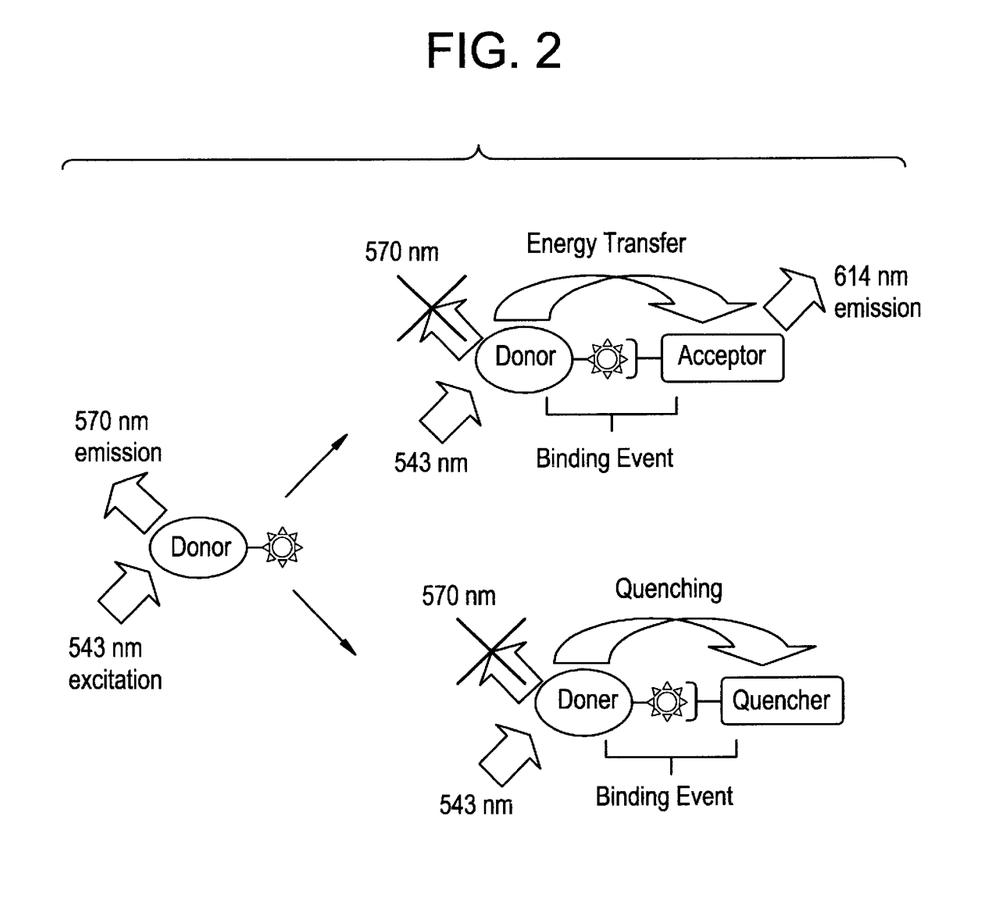
FIG. 2 is an illustration of the quenching mechanism employed in an embodiment of the invention.
Figure 3A:
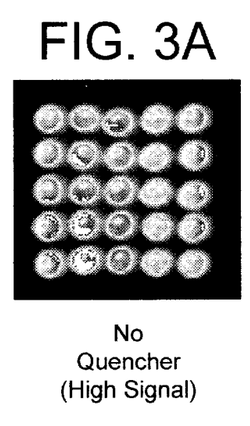
Figure 3B:
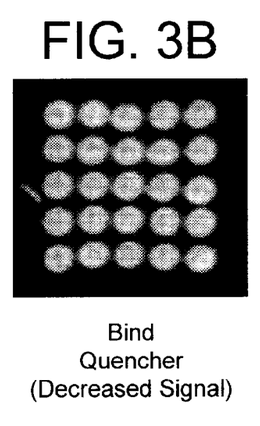
Figure 3C:
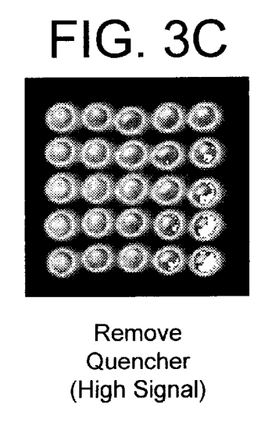
Figure 5:
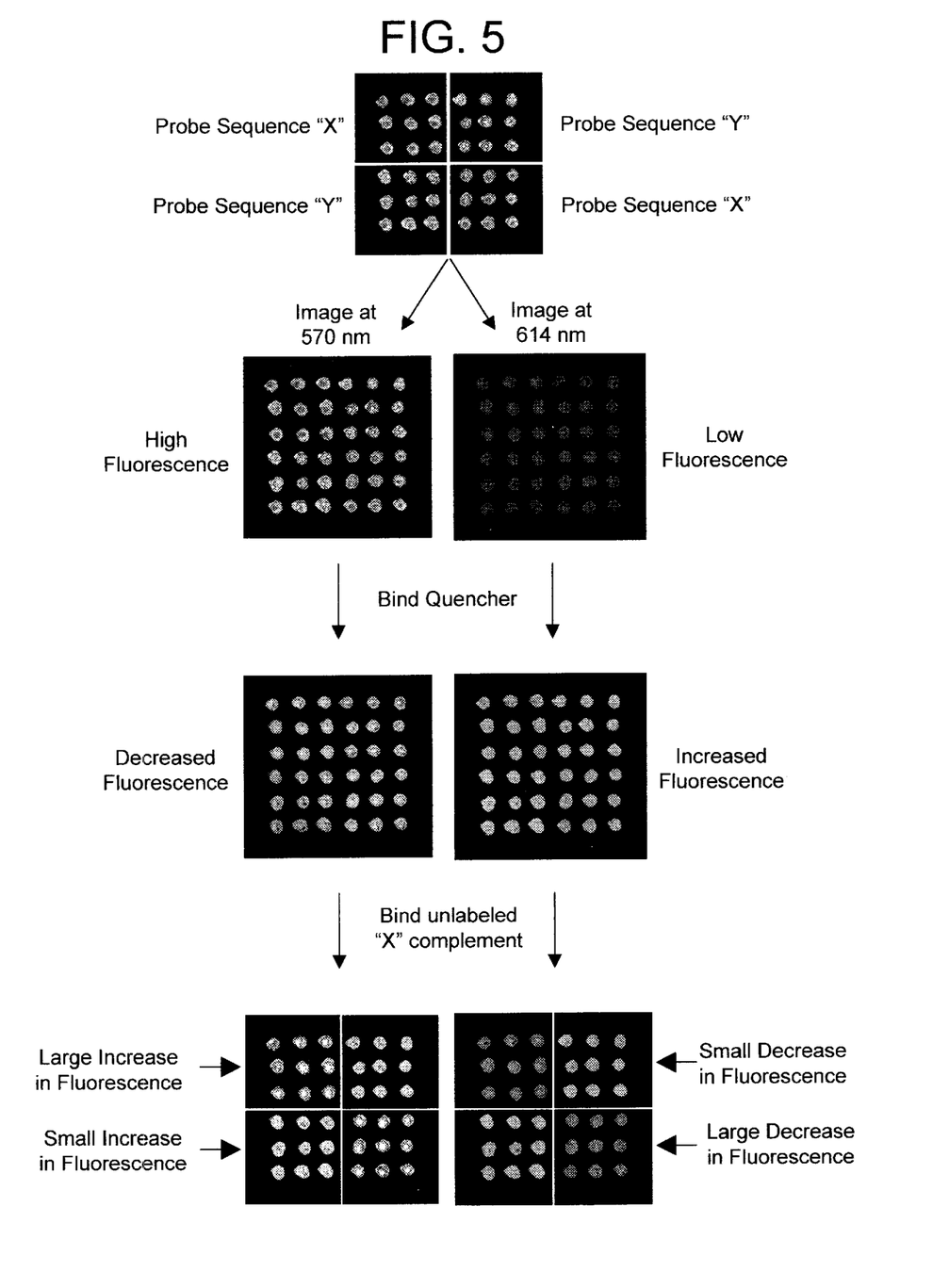
FIG. 5 is an illustration of the array shown in FIG. 4, demonstrating the effect of the displacement mechanism explained in FIG. 4, through use of fluorescent scanned images.

A schematic explanation of the binding events and fluorescence of the arrays depicted in FIGS. 3 and 5. FIG. 2 illustrates two possible, but non-exhaustive, incarnations of the present invention. In fluorescence quenching, the fluorescence intensity from a donor fluorophore decreases when a quencher is brought in close proximity by a binding event (e.g., hybridization of a probe to a target). Similarly for FRET, the binding of an acceptor in close proximity to the donor decreases the donor fluorescence intensity, and also results in an increase in acceptor emission. Thus, this scheme allows analysis of a binding event using two separate channels or signals. As shown in FIG. 2, for example, the emitter or donor moiety naturally emits or fluoresces at a certain wavelength of 570 nm, when excited by energy at 543 nm. In one path, energy transfers from the donor moiety to the acceptor moiety, which in this example, then emits at a wavelength of 614 nm. Alternatively, in another path, no emission occurs because the quencher has quenched the energy for an emission.

The three panels in FIG. 3 demonstrate that the quenching process is reversible. In FIG. 3($a$), a DNA array containing a Cy3-labeled probe sequence was prepared and imaged using 543 nm excitation and 570 nm emission. (Other light wavelengths that can be potentially applied range from about 300 nm to 1500 nm.) With no quencher the array emits at high signal. The array was then exposed to a solution containing a dabcyl-labeled perfectly complementary sequence. (Dabcyl is a non-fluorescent molecule that has been shown to be a "universal" quencher.) This resulted in a decrease in the Cy3 fluorescence of approximately 60%, as seen in FIG. 3($b$). Upon removal of the dabcyl quencher by soaking the slide in a formamide solution, the Cy3 signal returned to its initial value, as shown in FIG. 3($c$).

Figure 4:
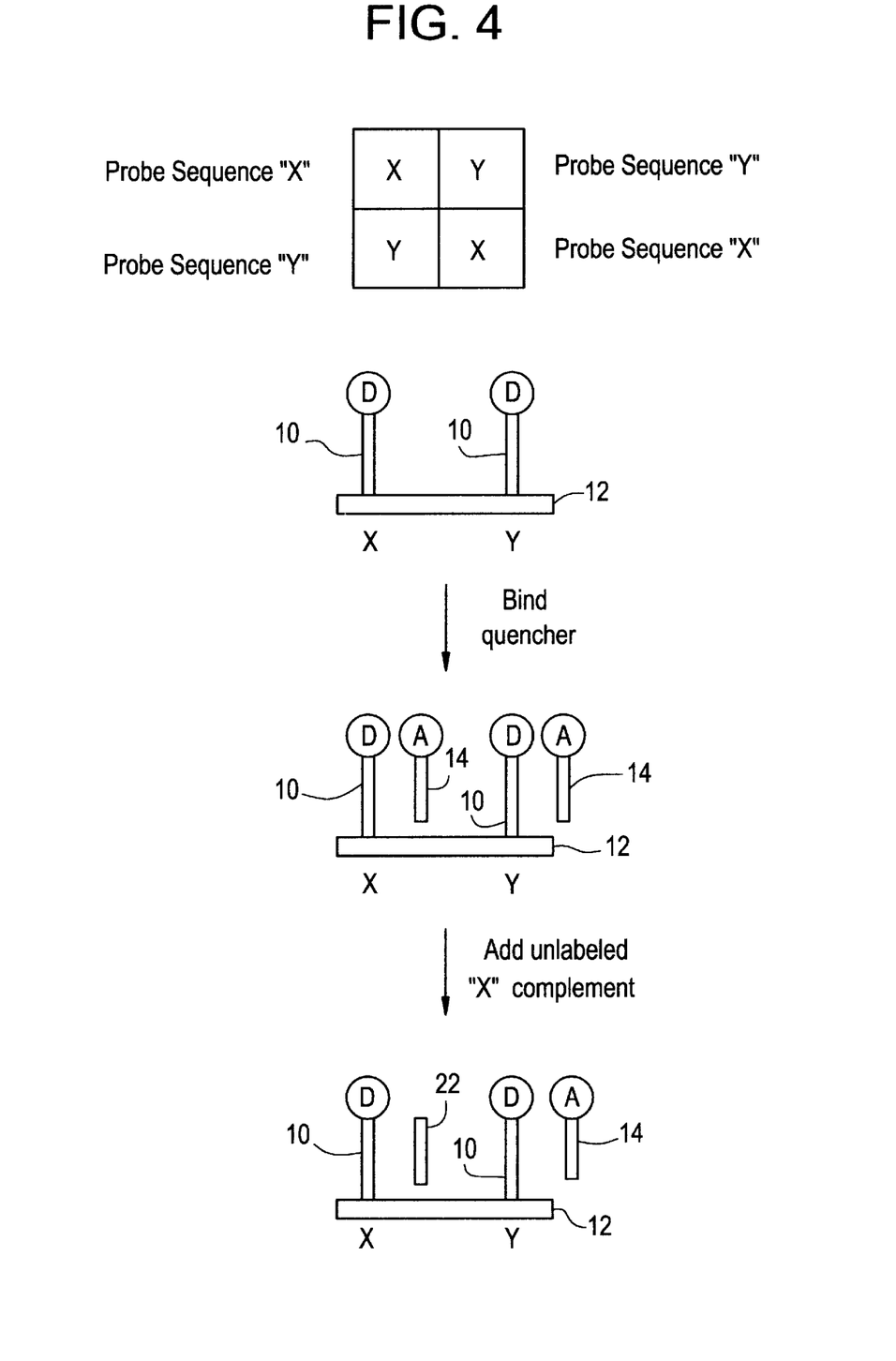
FIG. 4 is a schematic illustration of an array, and the comparative displacement mechanism for two different target nucleic acid sequences, X and Y.

To demonstrate the utility of this invention for the detection of single nucleotide polymorphisms, a model experiment was performed on a DNA array with an unlabeled oligonucleotide target. This experiment is schematically illustrated in FIG. 4 with the experimental data shown in FIG. 5. A DNA oligonucleotide array was prepared containing two different 15 mer oligonucleotide sequences (sequences "X" and "Y"), differing from each other by a single base at the $7^{th}$ nucleotide. (The spatial arrangement of these probe molecules is depicted at the top of FIGS. 4 and 5.) These probe molecules were labeled at their 5' end with an amine to allow attachment to the surface and at their 3' end with the fluorescent label Cy3. FIG. 5 shows the initial fluorescence images obtained from the array using 543 nm/570 nm and 594 nm/614 nm excitation/emission wavelengths to monitor the Cy3 and Rox signals, respectively. An acceptor sequence was then bound to the target sequences by exposing the surface to a solution of a Rox-labeled complementary sequence possessing an abasic site at the $7^{th}$ nucleotide. Analysis of the fluorescence images of the surface after this step reveals an approximate 60% decrease in fluorescence at 570 nm and a significant increase in fluorescence at 614 nm due to the presence of the Rox. As depicted in the last two panels of FIG. 5, exposure of the surface to a solution containing the unlabeled, perfectly complementary sequence to probe X resulted in clear discrimination between perfect match (probe X) and single base mismatch (probe Y) duplexes.

For analysis, we define the total discrimination factor between two oligonucleotides differing by at least one base-pair as the product of the discrimination factors in the donor and acceptor channels. For the donor channel (Cy3, image at 570 nm) the ratio of fluorescence intensity between match (probe X) and mismatch (probe Y) is 1.48; for the Rox channel the ratio between probe Y and probe X was 1.95. Therefore, the total discrimination factor 2.89 for single-base mismatch detection. It is anticipated that optimization of reaction conditions (e.g. salt concentration, temperature, formamide concentration) will lead to even further improvements in discrimination.

The invention is described in terms of FRET or fluorescence quenching terminology for ease of explanation, but that is not to limit the scope of this invention to only FRET pair mechanics or other fluorescence-based methodologies. The concept of mismatch discrimination described herein, and the general principle of having an emitter element and quencher element is compatible for use with a number of other analytical methods, such as displacement of radio-labeled quenchers, or mass spectrometry analysis of surface bound species after competitive displacement.

Although the present invention has been described by way of examples, it will be understood by those skilled in the art that the invention is not limited to the embodiments specifically disclosed, and that various modifications and variations can be made without departing from the spirit and scope of the invention. Therefore, unless changes otherwise depart from the scope of the invention as defined by the following claims, they should be construed as included herein.

We claim:

1. A method for detecting or identifying genetic polymorphisms, said method comprising:
proving (1) a set of first probes, each (i) having a nucleic acid sequence that is attached to a solid support, and (ii) differing from each other in at least one base location, and (2) a set of second probes, each having a nucleic acid sequence that incorporates at least one artificial mismatch site relative to a first probe, such that said first probe and second probe are bound to each other in a duplex;
providing each first probe with an emitter element, and each second probe with a quencher element;
hybridizing an unlabeled sample nucleic acid target to said duplex of first and second probes;
displacing said second probe from said duplex with said sample nucleic acid target, wherein said emitter element increases in emission intensity with such displacement.

2. The method according to claim 1, wherein each of said sample nucleic acid target is perfectly complementary to a number of said first probes.

3. The method according to claim 1, wherein each of said sample nucleic acid target is not perfectly complementary to a number of said first probes.

4. The method according to claim 1, wherein each nucleic acid sequence of said second probes has 1–5 artificial mismatch sites.

5. The method according to claim 4, wherein each artificial mismatch site is separated from one another by about 3–5 nucleotide positions.

6. The method according to claim 1, wherein said nucleic acid sequence of said first probes are attached to a solid support by covalent bonding.

7. The method according to claim 1, wherein said nucleic acid sequence of said first probes are attached to a solid support by non-covalent bonding.

8. The method according to claim 1, wherein said solid support is an article selected from a group consisting of porous substrates, non-porous substrates, three-dimensional surfaces, beads and planar surfaces.

9. The method according to claim 1, wherein said solid support is an article made from materials selected from a group consisting of glass, polymers, plastics, metals, and silicon.

10. The method according to claim 1, wherein said nucleic acid sequences of said first probes and said second probes each has a functional length of up to about 20–25 nucleotides.

11. The method according to claim 10, wherein said nucleic acid sequences of first probes and said second probes each has a functional length of about 14–19 nucleotides.

12. The method according to claim 1, wherein said first probe sequences are selected from the group consisting of DNA, PNA, RNA, and mixtures of DNA, PNA and RNA.

13. The method according to claim 1, wherein said sample nucleic acid target displaces said second probe by a thermokinetic mechanism wherein said sample nucleic acid target is favored to hybridize with a perfectly complementary first probe.

14. The method according to claim 13, wherein a first duplex containing at least one artificial mismatch site is formed when said first probe hybridizes with said second probe, and a second duplex is formed when said same first probe hybridizes with a perfectly complementary sample nucleic acid target, and said second duplex has a thermodynamic stability greater than a thermodynamic stability of said first duplex.

15. The method according to claim 13, wherein said second duplex has a melting temperature ($T_m$) greater than a melting temperature of said first duplex.

16. The method according to claim 1, wherein said method is used in an analysis of gene expression.

17. A method for detecting genetic polymorphisms, said method comprising:
providing a plurality of DNA duplexes, each having a first nucleic acid sequence that is immobilized to a solid support and labeled with a fluorophore, and an attached second nucleic acid sequence that incorporates at least one mismatch site and is labeled with a fluorescence quencher;
exposing said first nucleic acid sequence to an unlabeled sample DNA sequence that is perfectly complementary to said first nucleic acid sequence;
dislodging said second nucleic acid sequence from said first nucleic acid sequence, thereby removing said quencher.

18. The method according to claim 17, wherein said exposure of said solid support to said sample DNA target occurs in solution.

19. The method according to claim 17, wherein said sample DNA target hybridizes with said first nucleic acid sequence at a temperature in the range from about 20° C. to 100° C.

20. The method according to claim 19, wherein said temperature ranges from about 25° C. to 55° C.

21. A method for detecting genetic polymorphisms, said method comprising:
immobilizing on a solid support a plurality of first oligonucleotide probes, each having a first nucleic acid sequence to which an emitting element is attached;
providing (1) a second probe having a second nucleic acid sequence, and (2) an unlabeled sample nucleic acid target; hybridizing under competitive conditions said second probe and said sample nucleic acid target to said first oligonucleotide, wherein said second probe binds to said first oligonucleotide probe and said quenching element reduces an emission from said emitting element when said sample nucleic acid target is not complementary.

22. The method according to claim 21, wherein each of said sample nucleic acid target is perfectly complementary to a number of said first oligonucleotide probes.

23. The method according to claim 21, wherein each of said sample nucleic acid target is not perfectly complementary to a number of said first oligonucleotide probes.

24. The method according to claim 21, wherein each nucleic acid sequence of said second oligonucleotide probes has 1–5 artificial mismatch sites.

25. The method according to claim 24, wherein each artificial mismatch site is separated from one another by about 3–5 nucleotide positions.

26. The method according to claim 21, wherein said nucleic acid sequence of said first oligonucleotide probes are attached to solid support by covalent bonding.

27. The method according to claim 21, wherein said nucleic acid sequence of said first oligonucleotide probes are attached to a solid support by non-covalent bonding.

28. The method according to claim 21, wherein said solid support is an article selected from a group consisting or porous substrates, non-porous substrates, three-dimensional surfaces, beads and planar surfaces.

29. The method according to claim 21, wherein said solid support is an article made from materials selected from a group consisting of glass, polymers, plastics, metals, and silicon.

30. The method according to claim 21, wherein said nucleic acid sequences of said first oligonucleotide probes and said second oligonucleotide probes each has a functional length of up to about 20–25 nucleotides.

31. The method according to claim 30, wherein said nucleic acid sequences of first oligonucleotide probes and said second oligonucleotide probes each has a functional length of about 14–19 nucleotides.

32. The method according to claim 21, wherein said first oligonucleotide probe sequences are selected from the group consisting of DNA, PNA, RNA, and mixtures of DNA, PNA and RNA.

33. The method according to claim 21, wherein said sample nucleic acid target displaces said second oligonucleotide probe by a thermo-kinetic mechanism wherein said sample nucleic acid target is favored to hybridize with a perfectly complementary first oligonucleotide probe.

34. The method according to claim 33, wherein a first duplex containing at least one artificial mismatch site is formed when said first oligonucleotide probe hybridizes with said second oligonucleotide probe, and a second duplex is formed when said same first oligonucleotide probe hybridizes with a perfectly complementary sample nucleic acid target, and said second duplex has a thermodynamic stability greater than a thermodynamic stability of said first duplex.

35. The method according to claim 33, wherein said second duplex has a melting temperature ($T_m$) greater than a melting temperature of said first duplex.

36. The method according to claim 21, wherein said method as used in an analysis of gene expression.

* * * * *

UNITED STATES PATENT AND TRADEMARK OFFICE
CERTIFICATE OF CORRECTION

PATENT NO. : 6,579,680 B2 Page 1 of 1
DATED : June 17, 2003
INVENTOR(S) : Anthony G. Frutos et al.

It is certified that error appears in the above-identified patent and that said Letters Patent is hereby corrected as shown below:

Column 14,
Line 53, after "sequence", please add -- that is hybridizable to said first nucleic acid sequence, and having at least one artificial mismatch site and a quenching element attached to said second nucleic acid sequence, --

Column 15,
Line 14, delete "or" and add -- of --

Signed and Sealed this

Seventeenth Day of February, 2004

JON W. DUDAS
*Acting Director of the United States Patent and Trademark Office*

```
                           SEQUENCE LISTING

<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: natural a/c, g/t or artificial g/5-nitrindole,
      g/abasic site mismatches

<400> SEQUENCE: 1
gggctatnac tatag                                                    15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: natural a/c, g/t or artificial g/5-nitrindole,
      g/abasic site mismatches

<400> SEQUENCE: 2
ctatagtnat agccc                                                    15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggctataac tatag                                                    15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

-continued

```
<222> LOCATION: (8)
<223> OTHER INFORMATION: 5-nitrindole or abasic site

<400> SEQUENCE: 4
ctatagtnat agccc                                                15
```